(12) United States Patent
Fech et al.

(10) Patent No.: US 9,878,126 B2
(45) Date of Patent: Jan. 30, 2018

(54) NOZZLE FOR THE SUPPLY OF BIOLOGICAL MATERIAL, IN PARTICULAR CELLS, MEDICAL DEVICE WITH SUCH A NOZZLE, USE OF A NOZZLE, METHOD FOR MIXING FLUIDS AND APPARATUS

(71) Applicant: ERBE Elektromedizin GmbH, Tuebingen (DE)

(72) Inventors: Andreas Fech, Tuebingen (DE); Klaus Fischer, Nagold (DE); Markus Enderle, Tuebingen (DE); Mara Szyrach, Zurich (CH)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 836 days.

(21) Appl. No.: 14/054,408

(22) Filed: Oct. 15, 2013

(65) Prior Publication Data
US 2014/0107620 A1    Apr. 17, 2014

(30) Foreign Application Priority Data
Oct. 16, 2012    (EP) ..................................... 12188674

(51) Int. Cl.
*A61M 31/00* (2006.01)
*A61M 37/00* (2006.01)
(Continued)

(52) U.S. Cl.
CPC ....... *A61M 25/0067* (2013.01); *B01F 5/0057* (2013.01); *B01F 13/0013* (2013.01);
(Continued)

(58) Field of Classification Search
CPC    A61B 2017/00522; A61M 2025/0073; A61M 25/0068; A61M 25/0071;
(Continued)

(56) References Cited

U.S. PATENT DOCUMENTS 6,047,861 A    4/2000  Vidal et al.
6,161,778 A  * 12/2000  Haruch ................. B05B 7/0458
                                                         239/290

(Continued)

FOREIGN PATENT DOCUMENTS

CN    2239296 Y    11/1996
EP    2163204 A1    3/2010
(Continued)

OTHER PUBLICATIONS

Office action in corresponding Russian Application No. 2013145967/14(071225), dated Sep. 2, 2015, 4 pages.
(Continued)

*Primary Examiner* — Jason Flick
(74) *Attorney, Agent, or Firm* — Fitch, Even, Tabin & Flannery LLP

(57) ABSTRACT

A nozzle for the supply of biological material, in particular tissue cells, having a mixing chamber (11) which is delimited by a proximal end surface (21) and a distal end surface (22) spaced apart from the proximal end surface (21), at least one nozzle opening (23) which is formed in the distal end surface (22), and at least two supply ducts (30, 40, 50) which discharge into the mixing chamber (11). A first supply duct (30) is arranged in the proximal end surface (21) and discharges into the mixing chamber (11) coaxially to the nozzle opening (23) and a second supply duct (40) has an inlet opening (42) which discharges into the mixing chamber (11) laterally, in particular tangentially at the distal end surface (22).

15 Claims, 5 Drawing Sheets

(51) Int. Cl.
*A61M 25/00* (2006.01)
*B05B 1/34* (2006.01)
*B05B 7/04* (2006.01)
*B05B 7/10* (2006.01)
*B01F 5/00* (2006.01)
*B01F 13/00* (2006.01)
*A61B 17/00* (2006.01)

(52) U.S. Cl.
CPC .......... *B05B 1/3426* (2013.01); *B05B 1/3436* (2013.01); *B05B 7/0483* (2013.01); *B05B 7/10* (2013.01); *A61B 2017/00495* (2013.01); *A61B 2017/00522* (2013.01); *A61M 2025/0073* (2013.01); *B05B 1/3442* (2013.01)

(58) Field of Classification Search
CPC ............ A61M 25/0067; B01F 13/0013; B01F 5/0057; B01F 5/00; B01F 2005/0005; B01F 2005/0017; B01F 2005/002; B01F 2005/0037; B01F 2005/004; B01F 2005/0045; B01F 2005/0051; B01F 2005/0054; B01F 5/006; B01F 5/0062; B01F 5/0068; B01F 5/04; B05B 1/3426; B05B 1/3436; B05B 1/3442; B05B 7/0483; B05B 7/10; B05B 1/00; B05B 1/02; B05B 1/06; B05B 1/34
USPC .......................................................... 604/518
See application file for complete search history.

(56) References Cited

U.S. PATENT DOCUMENTS

| | | |
|---|---|---|
| 6,454,786 B1 | 9/2002 | Holm et al. |
| 6,835,186 B1 | 12/2004 | Pennington et al. |
| 2006/0280690 A1 | 12/2006 | Wright |
| 2008/0161757 A1 | 7/2008 | Nayak et al. |
| 2012/0158048 A1 | 6/2012 | Roush et al. |
| 2012/0218857 A1* | 8/2012 | Ocola .................. B01F 5/0655 366/336 |

FOREIGN PATENT DOCUMENTS

| | | |
|---|---|---|
| JP | 2001-505787 A | 5/2001 |
| JP | 2004141800 A | 5/2004 |
| WO | 98/20931 A1 | 5/1998 |
| WO | 2012/87378 A1 | 6/2012 |

OTHER PUBLICATIONS

Office action in corresponding European Application No. 12 188 674.1, dated Jun. 15, 2015, 6 pages.
Notice of Rejection from corresponding Japanese Application No. 2013-213375, dated Dec. 24, 2015, 6 pages.
Notification of Reason for Refusal in corresponding Korea Application No. 10-2013-0121954, dated Apr. 21, 2015, 8 pages.
Notification of Final Rejection in corresponding Korea Application No. 10-2013-0121954, dated Nov. 26, 2015, 5 pages.
Notification of Final Rejection in corresponding Korea Application No. 10-2013-0121954, dated Mar. 31, 2016, 5 pages.
Search Report for corresponding Japanese Application No. 2013-213375, dated Sep. 18, 2014, 32 pages.
European Search Report, related Application No. EP 12188674.1 dated Jun. 13, 2013, 7 pages.
Notice of Rejection from corresponding Japanese Application No. 2013-213375, dated Sep. 11, 2014.
Office action in corresponding European Application No. 12 188 674.1, dated Jul. 12, 2016, 7 pages.
First search in corresponding Chinese Application No. 201310481597.1, dated Aug. 25, 2015, 1 page.
First office action in corresponding Chinese Application No. 201310481597.1, dated Sep. 6, 2015, 10 pages.
Supplemental search in corresponding Chinese Application No. 201310481597.1, dated May 5, 2016, 1 page.
Second office action in corresponding Chinese Application No. 201310481597.1, dated May 16, 2016, 20 pages.
National Standard Gost 8.361-79, dated 1979, 16 pages.
Office action in corresponding Russian Application No. 2013145967/14(071225), dated Apr. 27, 2015, 6 pages.
Third office action and search report in corresponding Chinese Application No. 201310481597.1, dated Dec. 5, 2016, 21 pages.
Notice of Reasons for Refusal in corresponding Japanese Application No. 2013-213375, dated May 27, 2015, 4 pages.
Report of Reconsideration by Examiner before Appeal in corresponding Japanese Application No. 2013-213375, dated Aug. 12, 2016, 4 pages.
Fourth Office Action and Search for corresponding Chinese Application No. 201310481597.1, dated May 18, 2017, 26 pages.
Office Action in corresponding Chinese Application No. 201310481597.1, dated Sep. 20, 2017, 16 pages.

\* cited by examiner

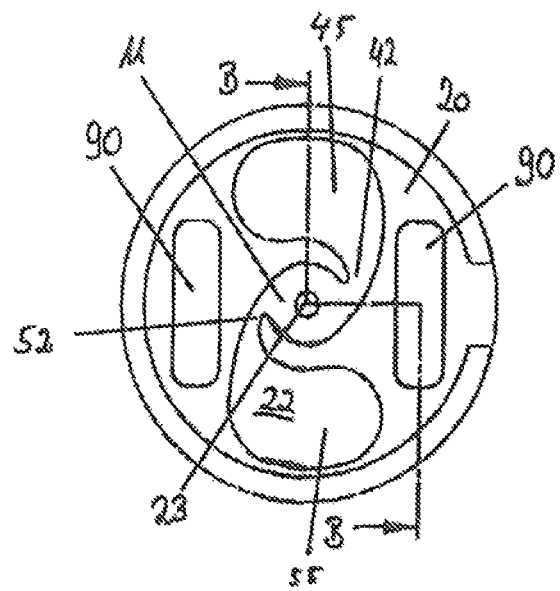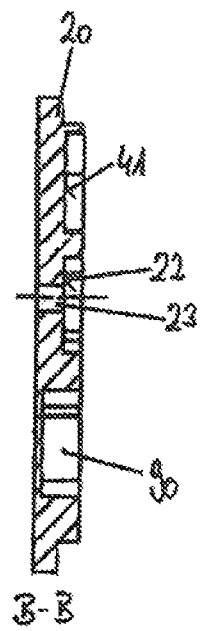
Fig. 4a　　　　　　Fig. 4b
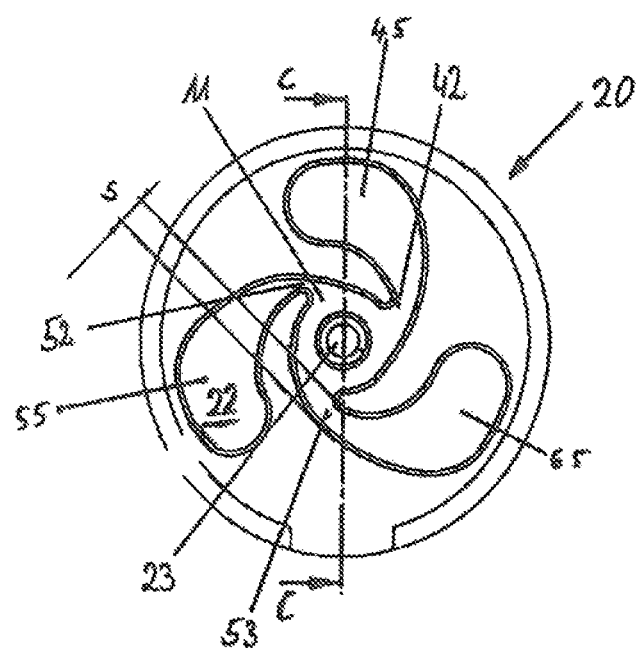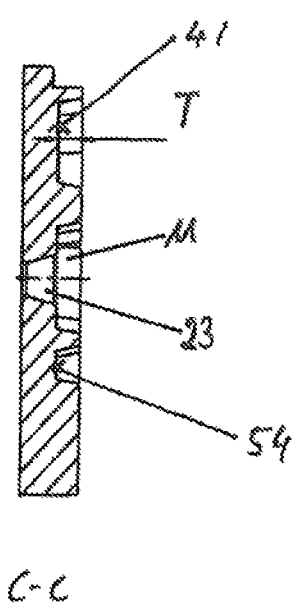
Fig. 5a　　　　　　Fig. 5b

NOZZLE FOR THE SUPPLY OF BIOLOGICAL MATERIAL, IN PARTICULAR CELLS, MEDICAL DEVICE WITH SUCH A NOZZLE, USE OF A NOZZLE, METHOD FOR MIXING FLUIDS AND APPARATUS

RELATED APPLICATION(S)

This application claims the benefit of European Patent Application No. EP 12188674.1 filed Oct. 16, 2012, the contents of which are incorporated herein by reference as if fully rewritten herein.

TECHNICAL FIELD

The invention relates to a nozzle for the supply of biological material, in particular cells. The invention furthermore relates to a medical device, in particular a surgical instrument, with such a nozzle and the use of a nozzle, a method for mixing fluids and an apparatus.

BACKGROUND

EP 2 163 204 A1 describes a nozzle for mixing and administering a biological adhesive, in particular fibrin glue. The nozzle comprises two supply ducts arranged parallel in a probe which discharge into a shared mixing chamber at the proximal end of the nozzle.

In the case of the known nozzle, both supply ducts discharge into the mixing chamber parallel to one another. This has the result that a uniform pressure level is set in the mixing chamber which acts on all the individual flows which reach the mixing chamber. Since different substances, which also as a result differ in terms of their viscosity, are fed into the mixing chamber, fluctuating mixing ratios emerge. The pressure level in the mixing chamber is furthermore set to the relatively higher value of the individual pressures of the two substances supplied via the separate supply ducts. A relatively high pressure thus arises in the mixing chamber which is undesirable in certain applications, for example, in the supply of cell material. In concrete terms, biological substances can be damaged by the high pressure.

In the case of the nozzle according to EP 2 163 204, an insert is furthermore arranged in the mixing chamber, which insert should bring about an improved mixing of the two substances fed into the mixing chamber. The insert has deflection elements, as a result of which a rotation of the fluids which flow into the mixing chamber is brought about within the mixing chamber. Shear stresses thus arise in both fluids which can have a damaging effect on biological material, in particular cells.

SUMMARY

The invention is based on the object of indicating a nozzle for the supply of biological material, in particular cells, which enables an improved and pressure-friendly mixing of fluid flows. The object furthermore lies in indicating a nozzle which can be easily switched between different forms of fluid flow. A further object of the invention is to indicate a medical device, a surgical instrument with such a nozzle and the use of a nozzle, a method for mixing fluids and a surgical apparatus for open-loop and closed-loop control of the surgical instrument. The surgical instrument according to the invention can be used in an endoscope.

The invention is thus based on the concept of indicating a nozzle for the supply of biological material, in particular cells, with a mixing chamber which is delimited by a proximal end surface and a distal end surface spaced apart from the proximal end surface. The nozzle has at least one nozzle opening which is formed in the distal end surface. The nozzle furthermore comprises at least two supply ducts which discharge into the mixing chamber. In this case, a first supply duct is arranged in the proximal end surface and discharges into the mixing chamber coaxially to the nozzle opening. A second supply duct has an inlet opening which discharges into the mixing chamber laterally, in particular tangentially, at the distal end surface.

The nozzle according to the invention has two particular features which enable an improved and pressure-friendly mixing of two fluids. On one hand, it is provided that the first supply duct discharges into the mixing chamber coaxially to the nozzle opening. It is thus achieved that the fluid flow, which reaches the mixing chamber via the first supply duct, is fed in a straight line, i.e. without deflection, through the mixing chamber to the nozzle opening. As a result of the arrangement according to the invention of the first supply duct, the generation of shear forces within this supply duct is well-nigh avoided. It is avoided that shear forces act on the fluid fed via the first supply duct into the mixing chamber. As a result of the reduction in the generation of shear forces, the risk of damage to, for example, cells, which the fluid fed in the first supply duct contains, is reduced, preferably almost entirely eliminated. On the other hand, it is provided in contrast to known nozzles that, in addition to the first coaxially arranged supply duct, at least one second supply duct discharges laterally into the mixing chamber. The arrangement according to the invention and the configuration according to the invention of the supply ducts improves mixing and additionally makes it possible to influence, preferably reduce, the pressure ratios in the mixing chamber. Due to the fact that the fluid supplied via the second supply duct flows laterally, in particular tangentially, into the mixing chamber, there arises in the mixing chamber a substantially rotating flow of the second fluid supplied via the second supply duct with respect to the first fluid which flows via the first supply duct arranged coaxially with respect to the nozzle opening into the mixing chamber. This leads to a particularly gentle mixing through of the two fluids, which is furthermore achieved at significantly lower supply pressures in at least one of the two supply ducts than is the case with previously known nozzles of an identical size.

It has proven to be advantageous for the careful supply of biological material if the mixing of the fluids takes place immediately in front of the nozzle opening, i.e. at as short a distance as possible in front of the exit from the nozzle. The nozzle according to the invention makes this possible in that the inlet opening of the second supply duct discharges into the mixing chamber at the distal end surface. The mixing of cell material, for example, cells in a solution, with a carrier fluid is therefore carried out as late as possible, i.e. in particular immediately in front of the nozzle opening. The cells are therefore exposed to flow turbulence and pressure for a comparatively short period of time during mixing. This protects the cells since in particular the time influence of damaging shear stresses is reduced.

A further advantage of the nozzle according to the invention is produced by the arrangement of the inlet opening of the second supply duct. In concrete terms, it is provided that the inlet opening discharges laterally into the mixing chamber. The fluid which flows via the lateral inlet opening into the mixing chamber therefore strikes the fluid flowing in axially from the first supply duct at an angle. The fluid flow of the second fluid, which is fed in the second supply duct, is thus deflected prior to supply into the mixing chamber. The formation according to the invention of the inlet opening enables a reduction in the static pressure of the second fluid. As a result of this formation according to the invention of the inlet opening, it is possible that both fluids, the second and the first fluid, are supplied to the mixing chamber with different pressures. This is, for example, not the case with the supply duct arrangement according to EP 2 163 204 A1.

In one preferred variant of the nozzle according to the invention, it is provided that the mixing chamber has a length L which is at most 500 µm, in particular at most 250 µm, preferably at most 150 µm. It is particularly preferred if length L of the mixing chamber is at most 100 µm, in particular at most 75 µm, preferably at most 50 µm, more preferably at most 30 µm. Length L of the mixing chamber corresponds here to the distance between the proximal end surface and the distal end surface. The comparatively short length of the mixing chamber brings about as late as possible mixing of the fluids fed into the mixing chamber because they are fed separately for a maximally long distance in the supply ducts and are mixed in the mixing chamber at as short a distance as possible, preferably immediately, in front of the nozzle opening. A careful supply of cells is thus achieved. As a result of short length L of the mixing chamber and the resultant short mixing time, the crosslinking of the supplied fluids is additionally influenced, preferably largely avoided. The crosslinking process of the supplied fluids begins jointly with the mixing process, i.e. at the point in time at which the fluids meet one another. As a result of the crosslinking of the fluids, a fluid mixture is produced, with changed properties, for example, significantly higher viscosity which leads to a change in pressure, in particular to an increase in pressure. As a result of crosslinking and the associated change in state of the material, for example, polymer-like, elastic substances can be produced, as a result of which the risk of nozzle blocking is significantly increased. The crosslinking of the supplied fluids should ideally only begin after its exit from the nozzle. The length of the mixing chamber and the outlet opening of the nozzle is thus kept as small as possible according to the invention.

The length of the mixing chamber is preferably smaller, in particular very much smaller than the total length of the nozzle. The nozzle extends from the distal end of supply lines to the outlet surface of the nozzle opening. In other words, the nozzle has a total length which extends through the distance between the distal end of the supply line and a distal end surface in which the outlet side of the nozzle opening is arranged. The separately guided supply ducts occupy the majority of the total length of the nozzle. These extend from the distal end of the supply lines to the inlet chamber which forms the transition to the mixing chamber. The supply ducts are guided continuously separately in particular across the majority of the total length of the nozzle. There is preferably no connection between the supply ducts on the section between the supply lines and the mixing chamber. The supply ducts are merged or fluid-connected exclusively on entry into the mixing chamber.

The mixing chamber and the nozzle opening preferably extend along a relatively smaller portion of the total length of the nozzle. In concrete terms, the cumulative length from the mixing chamber length and the nozzle opening length can at most correspond to a third, in particular at most a fifth, preferably at most a tenth, of the total length of the nozzle. The nozzle opening can be formed by a cylinder arranged coaxially to the longitudinal axis of the nozzle. The nozzle opening can also have a portion which is formed by the form of a cone which increases in size in the direction of the distal end surface of the nozzle.

Reference should be made at this point to the fact that the medical direction indications relate proximally and distally to the user of the nozzle or the medical device with the nozzle as the reference point. Components located further away from the user are arranged distally. Components closer to the user are, however, arranged proximally.

The lateral inlet opening can have a depth T which corresponds to length L of the mixing chamber. In other words, the lateral inlet opening can extend across the entire length of the mixing chamber. The configuration of a very small mixing chamber thus becomes possible which is advantageous for the careful supply of biological material, in particular cells. A compact and structurally simple design of the nozzle is furthermore achieved in this manner.

According to another embodiment of the nozzle according to the invention, the distal end surface of the mixing chamber is arranged perpendicular to a longitudinal axis of the second supply duct. As a result, a compact design of the nozzle becomes possible. The second fluid, which flows through the second supply duct, is, as a result of the distal end surface of the mixing chamber arranged perpendicular to the longitudinal axis, deflected with an angle of 90° before it is supplied to the mixing chamber.

A compact design of the nozzle can furthermore be achieved in that the supply ducts are arranged parallel to one another at least in sections.

The lateral inlet opening has a rectangular cross-sectional profile. In this case, one of the four lateral surfaces of the cross-sectional profile can be formed by the distal end surface of the mixing chamber. The rectangular cross-sectional profile enables a simplified structural design and simplified production of the nozzle. The cross-sectional surface of the inlet opening can be formed to be very small. This leads to an increase in the flow speed of the fluid in the second supply duct, as a result of which the pressure, in particular the static pressure of the second fluid fed in the second supply duct is reduced prior to the mixing chamber.

In the case of one special embodiment, the above-mentioned effect can be amplified in that the lateral inlet opening tapers in the direction of the mixing chamber. In concrete terms, the lateral inlet opening can have two curved lateral surfaces which converge at the mixing chamber. The curved lateral surfaces can be arranged at a right angle to the distal end surface of the mixing chamber. As a result of the tapering, which is configured in one special configuration as two converging, curved lateral surfaces, it is achieved that the fluid which flows in the second supply duct is accelerated immediately before flowing into the mixing chamber. The static pressure of the second fluid falls as a result. The second fluid therefore flows with a relatively low pressure into the mixing chamber so that it is avoided that the first fluid flowing axially through the mixing chamber is exposed to a pressure which can damage biological material, in particular cells. The narrowing which is produced by the converging lateral surfaces forms an acceleration section for the second fluid along which the static pressure of the second fluid falls. The nozzle can thus advantageously be used to mix in cells, i.e., for example, cells found in suspensions, carefully with a carrier fluid. The mixture can subsequently leave the nozzle via the nozzle opening. The fluid which comprises the cells preferably flows through the first supply duct which is arranged coaxially to the nozzle opening. The carrier medium, in particular carrier fluid, reaches the mixing chamber laterally via the inlet opening of the second supply duct.

In the case of a further preferred embodiment of the nozzle according to the invention, it is provided that an outer lateral surface of the lateral inlet opening forms a continuous transition into an inner circumferential surface of the mixing chamber. In this manner, the fluid flowing through the inlet opening can be conducted into the mixing chamber with reduction or diminution of turbulence. The configuration of the inlet opening brings about that the fluid which flows through the inlet opening enters into the mixing chamber in a laminar form. This ensures consistent inflow and as a result consistent, careful, gradual mixing of the second fluid with the first fluid. In the context of the application, a constant, i.e. substantially barrier-free, transition is referred to as a continuous transition. The outer lateral surface therefore forms a substantially flush transition to the inner circumferential surface of the mixing chamber, in particular without having steps, edges or such barriers.

In a further configuration of the nozzle, at least one third supply duct with a further lateral inlet opening is provided. The further lateral inlet opening can discharge laterally into the mixing chamber at the distal end surface. In total, the nozzle can therefore comprise three supply ducts, wherein two supply ducts discharge via lateral inlet openings into the mixing chamber. A further supply duct reaches the mixing chamber axially, in particular coaxially to the nozzle opening. The supply ducts guided laterally into the mixing chamber, i.e. the second and third supply duct, preferably have inlet openings which are arranged at the distal end surface of the mixing chamber or directly adjoin the distal end surface of the mixing chamber. The range of applications of the nozzle is expanded by the third supply duct or the at least one further supply duct. More than two different fluids—simultaneously or at different times—can thus be mixed and supplied via the nozzle. The invention is furthermore not restricted to two or three supply ducts, rather also relates to a nozzle which has more than three, in particular four, five, six, seven or eight supply ducts. It is decisive that at least one of the supply ducts discharges into the mixing chamber coaxially to a nozzle opening.

The supply ducts and/or the mixing chamber and/or nozzle opening can in principle be formed in one piece or several pieces. A one-piece formation is characterised by good fluid imperviousness. On the other hand, a multi-piece formation of supply ducts and/or mixing chamber and/or nozzle opening has an improved production capacity.

The multi-piece formation of supply ducts and/or mixing chamber and/or nozzle opening can be achieved, for example, in that, as a further preferred configuration of the invention provides, the mixing chamber is formed in a mixing chamber plate which is arranged between a nozzle plate and a duct carrier. The duct carrier comprises the at least two supply ducts. It can alternatively be provided that the mixing chamber is formed in the nozzle plate. In the case of the nozzle according to the invention, the supply ducts can in principle be formed in a duct carrier and/or the nozzle opening can be formed in a nozzle plate, wherein the mixing chamber is formed in particular in the nozzle plate or a mixing chamber plate. The mixing chamber plate is arranged between the nozzle plate and the duct carrier. In a further design, the mixing chamber is formed in the duct carrier (distal end surface).

The mixing chamber plate preferably has a plate thickness which corresponds to the length of the mixing chamber, in particular the depth of the inlet opening. The mixing chamber plate can be formed in one piece, in particular integrally with the nozzle plate. In other words, the nozzle plate can at least in sections form the mixing chamber plate or the mixing chamber can be formed in the nozzle plate.

In a different embodiment, the mixing chamber can be formed in the duct carrier. It is then a component of the duct carrier. The distal end surface of the duct carrier and the distal end surface of the mixing chamber can then be one and the same end surface. It is also possible that the distal end surface of the duct carrier has an annular groove which can accommodate the nozzle plate.

In the case of the nozzle according to the invention, a temperature control duct can furthermore be provided which is adapted such that temperature control can be performed for a fluid flowing through at least one supply duct. The temperature control duct preferably comprises a supply line and a return line which can be connected to a closed temperature control circuit. The temperature control duct can be arranged directly adjacent to the mixing chamber and/or to the supply ducts. The temperature control duct preferably runs parallel to the supply ducts. For example, the viscosity of the fluids can be influenced by the temperature control, i.e. heating or cooling, of the nozzle, in particular the fluids flowing through the supply ducts or at least one of the fluids flowing through the supply ducts. The viscosity of at least one of the fluids fed through the supply ducts can thus be reduced via a temperature increase. This has the result that the shear forces which occur in the mixing chamber are also reduced. The influencing of the temperature of the individual fluids in the supply ducts can furthermore lead to an improved mixing of the fluids or to an improved crosslinking of the substances contained in the fluids.

The nozzle can furthermore have an atomiser plate. The atomiser plate can be connected distally to the nozzle plate and have an atomiser opening arranged coaxially to the nozzle opening. Moreover, at least one atomiser duct can be formed in the atomiser plate and connect the atomiser opening to a gas supply duct. The atomiser duct preferably discharges tangentially into the atomiser opening. Gas can thus additionally be supplied to the fluid jet exiting from the nozzle, which gas enables atomisation, in particular aerosol formation, of the exiting fluid.

According to a further aspect, the invention is based on the concept of indicating a nozzle for medical purposes with a mixing chamber which is delimited by a proximal end surface and a distal end surface spaced apart from the proximal end surface. The nozzle has at least one nozzle opening which is arranged in the distal end surface. The mixing chamber has a substantially cylindrical inner contour with at least two inlet openings which discharge into the mixing chamber laterally, in particular tangentially. The inlet openings are in each case fluid-connected to a supply duct. The inlet openings have different or the same cross-sectional surfaces.

The average entry speed of the fluid at the given volumetric flow which flows through the inlet opening into the mixing chamber is determined by the cross-sectional surface of the inlet opening. It is thus possible to introduce different or identical fluids with different or identical volumetric flows with the same, identical average entry speed into the mixing chamber. To this end, the ratio of the cross-sectional surfaces of the inlet openings of the different supply ducts is configured in accordance with the ratio of the volumetric flows of the fluids which flow through the different supply ducts. In other words, two or more fluids are merged in a defined volumetric ratio, i.e. in a specified ratio of the volumetric flows. In this case, the cross-sectional surfaces of the inlet openings are configured such that the same average entry speed of all the separately supplied fluids into the mixing chamber is achieved independently of the mixture ratio or independently of the magnitudes of the fluid flows. If, for example, a mixture ratio of 1 to 4 of the fluid of the second supply duct to the fluid in the third supply duct is required, this requires a cross-sectional surface of the inlet opening of the third supply duct which is 4 times larger while maintaining the same average entry speed of the fluids into the mixing chamber. In the case of a mixture ratio of 1:1, the cross-sectional surfaces of the inlet openings are of equal size.

In order to achieve as careful as possible mixing of the fluids flowing through the supply ducts offset radially to the outside with the fluid which flows through the coaxially arranged supply duct, it is necessary that the fluids supplied from outside enter into the mixing chamber with an identical average flow speed. This enables a low-turbulence, ideally turbulence-free mixing of the fluids in the mixing chamber.

Fluids are characterised by their chemical and/or biological composition and the concentrations of their components. The same components means the same chemical and/or biological composition and the same concentrations of the components.

This type of nozzle enables the setting of different forms of fluid jet, i.e. the form of the fluid jet exiting from the nozzle opening. This is achieved with particular ease in the case of the nozzle according to the invention in that the fluid supply in the various supply ducts is subject to open-loop or closed-loop control by means of an open-loop or closed-loop control unit of an apparatus to which a surgical instrument with a nozzle according to the invention is connected. In order to produce a conical jet when exiting from the nozzle opening, a fluid is supplied exclusively through a supply duct offset radially to the outside, for example, the second or third supply duct. This conical jet or the action of this conical jet on the tissue to be treated can be amplified by the additional supply of a fluid through the first supply duct. The sole supply of a fluid through the first supply duct produces a cylindrical full jet.

Reference should be made at this point to the fact that the cross-sectional dimensions of the inlet openings do not only refer to rectangular cross-sections, rather generally to polygonal or round or a combination of angular and round cross-sectional forms of the inlet openings.

With the present application, the nozzle for the supply of biological material and the nozzle for medical purposes are disclosed both separately, i.e. distinctly from one another, and in combination. The form, conical form, cylindrical full jet or a mixed form of both forms of jet of the fluid jet exiting from the nozzle opening can additionally be produced by the nozzle explained above for the supply of biological material.

The advantages and preferred further developments stated in the context of the nozzle for the supply of biological material also apply to the nozzle for medical purposes which enables easy setting of different forms of fluid jet.

Moreover, a further aspect of the invention lies in indicating a medical device, in particular a surgical instrument, with one of the above-mentioned nozzles.

BRIEF DESCRIPTION OF THE DRAWINGS

The invention is explained in greater detail below on the basis of exemplary embodiments with reference to the enclosed, schematic drawings. In these drawings:

FIG. 4a shows a top view of a nozzle plate with an integrated mixing chamber according to a further preferred exemplary embodiment, wherein temperature control ducts are provided;

FIG. 4b shows a cross-sectional view of the nozzle plate according to FIG. 4a along line B-B;

FIG. 5a shows a top view of a nozzle plate with an integrated mixing edge according to a further preferred exemplary embodiment, in the case of which three inlet openings into the mixing chamber are provided;

FIG. 5b shows a cross-sectional view of the nozzle plate according to FIG. 5a along line C-C;

DETAILED DESCRIPTION

Figure 1:
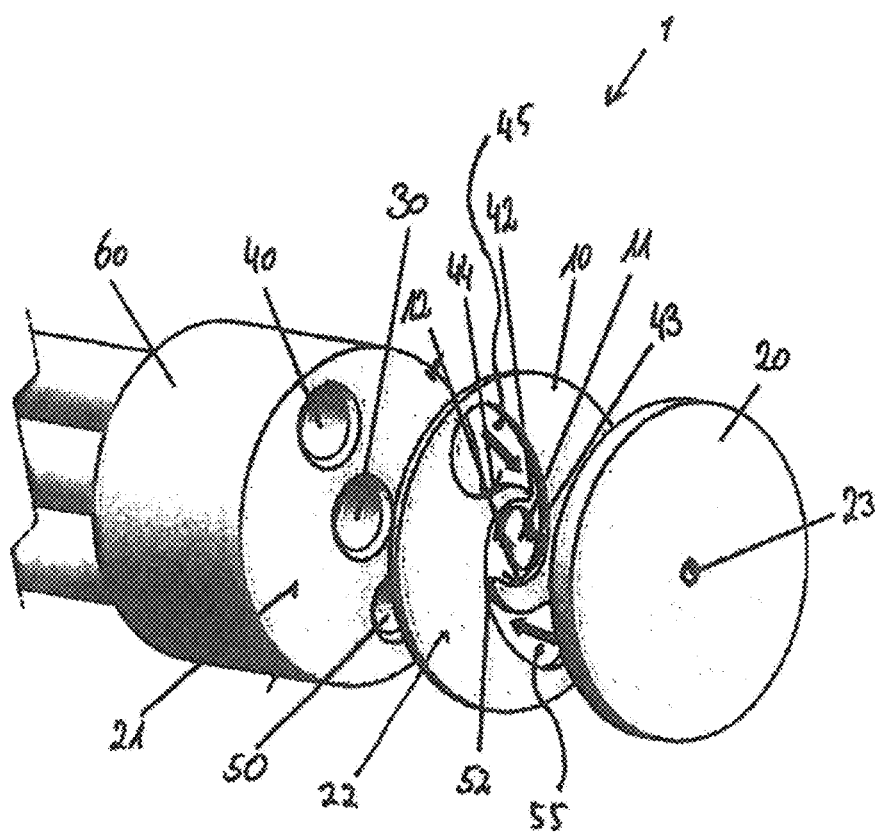
FIG. 1 shows a perspective exploded view of a nozzle according to the invention with three supply ducts according to one preferred exemplary embodiment.

Nozzle 1 according to the exemplary embodiment according to FIG. 1 is suitable for the supply of biological material and can be used in particular for the supply of cells. Nozzle 1 can be part of a medical device, in particular of a surgical instrument. Nozzle 1 is preferably part of a water jet applicator which is in particular also suitable for the careful supply of cells.

The nozzle generally has a mixing chamber 11, a nozzle opening 23 and at least two supply ducts 30, 40. Supply ducts 30, 40 discharge into mixing chamber 11. Supply ducts 30, 40 in a proximal end surface 21, which delimits mixing chamber 11 in the proximal direction, preferably discharge into mixing chamber 11. Mixing chamber 11 furthermore has a distal end surface 22 which delimits mixing chamber 11 in the distal direction. In other words, mixing chamber 11 is formed between proximal end surface 21 and distal end surface 22. Proceeding from distal end surface 22, nozzle opening 23 begins and extends away therefrom.

In proximal end surface 21, at least one first supply duct 30 discharges into mixing chamber 11. First supply duct 30 is furthermore arranged coaxially to nozzle opening 23 or is flush with nozzle opening 23.

A second supply duct 40 which comprises an inlet chamber 45 discharges into mixing chamber 11 offset radially to the outside in relation to the first supply duct. To this end, it is provided that inlet chamber 45 has an inlet opening 42 which discharges, in particular tangentially, into mixing chamber 11. In particular, second supply duct 40 discharges via inlet opening 42 immediately in front of nozzle opening 23 into mixing chamber 11. Inlet opening 42 is arranged radially to the outside in relation to nozzle opening 23, radially to the inside in relation to inlet chamber 45. Inlet opening 42 connects inlet chamber 45 of supply duct 40 to mixing chamber 11. This is achieved according to the invention in such a manner that inlet opening 42 forms a transition into mixing chamber 11 at distal end surface 22.

In concrete terms, it can be provided that second supply duct 40 has a deflection surface 41 which is arranged at the distal end of inlet chamber 45 of second supply duct 40. Deflection surface 41 delimits second supply duct 40 in the axial direction and brings about in particular a deflection of the fluid fed in second supply duct 40. Deflection surface 41 forms a transition to distal end surface 22 of mixing chamber 11 in the same plane or is formed with the same surface as distal end surface 22. Deflection surface 41 and distal end surface 22 are in principle located in the same plane. Deflection surface 41 and distal end surface 22 preferably form individual adjoining regions of a joint component surface.

Nozzle 1 according to FIG. 1 has a multi-piece structure. In principle, the nozzle can also have a one-piece structure. In particular, supply ducts 30, 40, 50, mixing chamber 11 and nozzle opening 23 can be formed seamlessly in one piece or can be integrated in a one-piece component.

The nozzle according to FIG. 1 has three supply ducts 30, 40, 50 which are arranged in a duct carrier 60. Supply ducts 30, 40, 50 preferably run parallel to one another in duct carrier 60. In particular, supply ducts 30, 40, 50 are arranged in a row, i.e. the longitudinal axes of supply ducts 30, 40, 50 intersect a common straight line which is arranged transverse to the longitudinal axes of supply ducts 30, 40, 50. Duct carrier 60 has at its distal end a surface which forms proximal end surface 21. Proximal end surface 21 delimits mixing chamber 11 in the proximal direction.

In the case of the exemplary embodiment according to FIG. 1, mixing chamber 11 is formed in mixing chamber plate 10. In the mounted state, mixing chamber plate 10 lies directly on proximal end surface 21 which proximally delimits mixing chamber 11 and to which duct carrier 60 is assigned. Mixing chamber 11 substantially has a cylindrical profile. In concrete terms, mixing chamber 11 has an inner circumferential surface 12 which has a circular arc curved shape in sections. Inner circumferential surface 12 is interrupted by inlet openings 42, 52.

Inner circumferential surface 12 of mixing chamber 11 forms a continuous transition to an outer lateral surface 43 of inlet opening 42. Outer lateral surface 43 can be arranged transverse, perpendicular, to supply ducts 30, 40, 50. The arrangement and the continuous transition of inner circumferential surface 12 to outer lateral surface 43 preferably applies to all inlet openings 42, 52 which discharge into mixing chamber 11. Inlet openings 42, 52 are, as is clearly apparent in FIGS. 2a, 4a and 5a, substantially arranged as drop-shaped cut-outs or gaps in mixing chamber plate 10 or nozzle plate 20 or duct carrier 60. The lateral surface of the drop-shaped cut-out which forms a continuous transition to inner circumferential surface 12 is referred to as outer lateral surface 43, i.e. the radius of curvature of outer lateral surface 43 changes continuously up to the value of the radius of curvature of inner circumferential surface 12. In other words, the radius of curvature changes continuously during the transition from outer lateral surface 43 of inlet opening 42, 52 to inner circumferential surface 12, i.e. including inner circumferential surface 12, of mixing chamber 11. The radius of curvature can reduce continuously or increase continuously, and it can also have constant regions. The transition of inner circumferential surface 12 to outer lateral surface 43 is formed to be continuous. Inlet opening 42, 52 furthermore has an inner lateral surface 44 which likewise has a curvature and ends in inner circumferential surface 12. The curvature of inner lateral surface 44 has a radius of curvature which differs from the radius of curvature of outer lateral surface 43. The radius of curvature of inner lateral surface 44 is preferably smaller than the radius of curvature of lateral surface 43 and reduces in the direction of inner circumferential surface 12. Proceeding from inlet chamber 45, inner lateral surface 44 extends in the direction of inlet opening 42, and forms a transition in a step-free manner or continuously to inner circumferential surface 12 which discharges in outer lateral surface 43 of inlet chamber 55. There is thus a substantially sickle-shaped arched web 46 between an inlet chamber 45, 55 and mixing chamber 11, inlet opening 42, 52 being arranged between the tip and outer lateral surface 43 of web 46. As is furthermore clearly apparent in FIG. 2a, outer lateral surface 43 and inner lateral surface 44 converge with one another. In other words, inlet opening 42 or inlet chamber 45 narrows in the direction of inlet opening 42. The same applies to inlet chamber 55 and inlet opening 52. Outer lateral surface 43 and inner lateral surface 44 form, in the radial direction, the lateral delimitations of inlet chambers 45, 55. In the axial direction, inlet chambers 45, 55 are delimited by proximal end surface 21 and distal end surface 22.

In principle, inlet openings 42, 52 can have different widths s1, s2. The same average flow speeds or flow speeds during entry of the fluids into mixing chamber 11 can be produced by different widths s1, s2 of inlet openings 42, 52 at the same depth T of the inlet opening. In order to achieve this, as described above, knowledge of the specified/required volumetric flow ratios of the fluids to one another which flow through separate inlet openings 42, 52 into mixing chamber 11, is necessary. It can, for example, be provided that first inlet opening 42 has a width s1 which is larger than width s2 of second inlet opening 52. This has the result that the fluid, which flows via first inlet opening 42 with a volumetric flow $Q_1$ into mixing chamber 11, flows with an average flow speed into mixing chamber 11 which is identical to the average flow speed of the second fluid which flows in via second inlet opening 52 with the relatively narrower opening width with a $Q_2<Q_1$. This facilitates the careful mixing of the fluids supplied via second supply duct 40 and third supply duct 50. The requirements for the identical average flow speed on entry into the mixing chamber of the two fluids supplied via inlet openings 42, 52 are not only the cross-sectional surfaces of the inlet openings, but also as described above the ratios in terms of volumetric flow.

Mixing chamber 11 is delimited in the distal direction by a distal end surface 22. Distal end surface 22 is preferably formed in a nozzle plate 20, which, in the case of the exemplary embodiment according to FIG. 1, is formed as a separate component. It is also possible, as FIGS. 2a and 2b, for example, show, that the nozzle plate has recesses or depressions in the form of mixing chamber 11 and inlet chambers 45, 55 as well as inlet openings 42, 52. In other words, mixing chamber plate 10 can be formed integrally with nozzle plate 20 or mixing chamber 11 in nozzle plate 20.

The surface arranged on the proximal side of nozzle plate 20 forms distal end surface 22 of mixing chamber 11. At the same time, distal end surface 22 forms a deflection surface 41, 51 for supply ducts 40, 50. This means that both inlet chambers 45, 55 and mixing chamber 11 are limited by distal end surface 22 or deflection surface 41, 51.

A nozzle opening 23 is formed in nozzle plate 20. Nozzle opening 23 is arranged coaxially to first supply duct 30. In particular, nozzle opening 23 is arranged coaxially to mixing chamber 11 and to first supply duct 30. Nozzle opening 23 has a cross-sectional diameter which is smaller than the cross-sectional diameter of first supply duct 30. It can generally be provided that first supply duct 30 and mixing chamber 11 have substantially the same cross-sectional diameter. The cross-sectional diameter of mixing chamber 11 can tend to have a slightly larger value than the cross-sectional diameter of first supply duct 30. The cross-sectional diameter of nozzle opening 23 can be smaller that the cross-sectional diameter of mixing chamber 11 and the cross-sectional diameter of supply duct 30.

Figure 3:
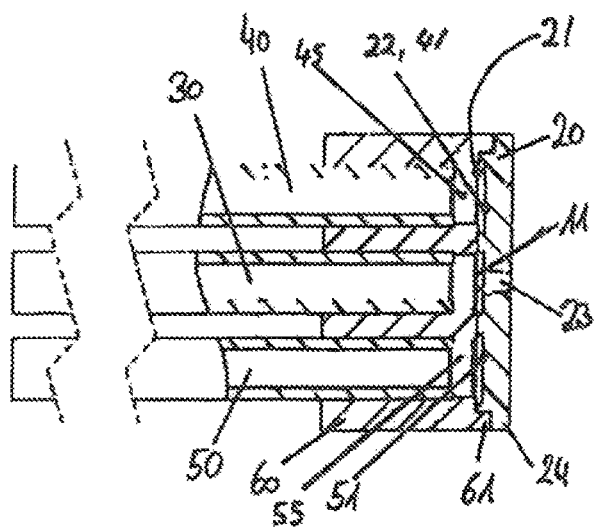
FIG. 3 shows a longitudinal sectional view through a nozzle according to the invention with the nozzle plate according to FIGS. 2a and 2b.

As is furthermore apparent in FIG. 3, both proximal end surface 21 and distal end surface 22 or deflection surfaces 41, 51 are arranged substantially perpendicular to the longitudinal axes of supply ducts 30, 40, 50. Deflection surfaces 41, 51 and distal end surface 22 and, where applicable, proximal end surface 21 can generally be arranged perpendicular to a longitudinal axis of second supply duct 40.

Embodiments are also possible in which distal end surface 22 is arranged at an angle, which differs from 90 degrees, to the longitudinal axis of nozzle 1 or of a supply duct 30, 40, 50. End surface 22 can be arranged in a range from 10 to 90 degrees, preferably 25 to 60 degrees.

FIG. 1 furthermore clearly shows that inlet openings 42, 52 have in each case a depth T which corresponds to length L of mixing chamber 11. In the case of the multi-piece embodiment according to FIG. 1, depth T of inlet opening 42, 52 and length L of mixing chamber 11 correspond to the plate thickness of mixing chamber plate 10. The length of mixing chamber 11 is in principle determined by the distance of proximal end surface 21 from distal end surface 22. Depth T of inlet opening 42, 52 is determined in the same manner, i.e. the distance between proximal end surface 21 and distal end surface 22 corresponds to depth T of inlet opening 42, 52.

Inlet chambers 45, 55 are adapted in terms of their dimensions to correspondingly assigned supply ducts 40, 50. Their cross-sectional shape and/or surface can deviate from the cross-sectional surface and/or cross-sectional shape of supply ducts 45, 50, wherein it is preferably larger. In one particular application, it can be advantageous if the cross-sectional surface and/or the cross-sectional shape of inlet chambers 45, 55 is identical to the cross-sectional shape and/or the cross-sectional surface of supply ducts 40, 50. In particular, inlet chambers 45, 55 form in each case the axial end portions of associated supply ducts 40, 50. Inlet chambers 45, 55 are delimited in the distal direction in each case by deflection surfaces 41, 51 or distal end surface 22 of mixing chamber 11.

The parallel arrangement of supply ducts 30, 40, 50 is clearly apparent in FIG. 3. It can furthermore be clearly seen that first supply duct 30 discharges axially into mixing chamber 11 and is aligned coaxially to nozzle opening 23. Both inlet chambers 45, 55 and mixing chamber 11 are formed to be comparatively narrow. It applies to all the exemplary embodiments that the length of mixing chamber 11 is selected to be as small as possible in order to enable short but efficient mixing immediately in front of nozzle opening 23. Length L of mixing chamber 11 is preferably at most 150 µm, in particular at most 120 µm, in particular at most 100 µm, in particular at most 70 µm, in particular at most 50 µm, in particular at most 40 µm, in particular at most 30 µm. Corresponding values apply to depth T of inlet openings 42, 52. Depth T of inlet openings 42, 52 preferably extends across entire length L of mixing chamber 11.

Reference should be made at this point to the fact that length L of mixing chamber 11 is substantially equivalent to the thickness of mixing chamber plate 10, at least if the nozzle has a separate mixing chamber plate 10, i.e. separated from nozzle plate 20.

Supply ducts 30, 40, 50 are arranged in a duct carrier 60 or held in a duct carrier 60. Duct carrier encloses at least in sections supply ducts 30, 40, 50, preferably the distal end portions of supply ducts 30, 40, 50. Duct carrier 60 can have a cylindrical outer contour. A circular recess can be provided at one distal end of duct carrier 60 so that duct carrier 60 has an annular rail 61 at the distal end. Adapted to the circular recess or annular rail 61, nozzle plate 20 can have a shoulder 24 which in the mounted state bears against rail 61. In the region of shoulder 24, nozzle plate 20 has an outer diameter which corresponds to the outer diameter of duct carrier 60. Outside of shoulder 24, i.e. in a mixing chamber portion, nozzle plate 20 has, however, a reduced outer diameter which corresponds to the cylindrical inner diameter of duct carrier 60 in the region of rail 61. Nozzle plate 20 can thus be placed in the manner of a cover, in particular in a positive-locking manner, onto duct carrier 60.

FIGS. 4a and 4b show a further exemplary embodiment of a nozzle plate 20 for a nozzle according to the invention. Nozzle plate 20 contains a mixing chamber 11 and two inlet chambers 45, 55 with inlet openings 42, 52 which discharge into mixing chamber 11. In particular, inlet openings 42, 52 discharge tangentially into mixing chamber 11. This means that outer lateral surfaces 43 of inlet openings 42, 52 or inlet chambers 45, 55 form a continuous transition to the inner circumferential surface of mixing chamber 11. This applies to all the exemplary embodiments.

Figures 2A, 2B:
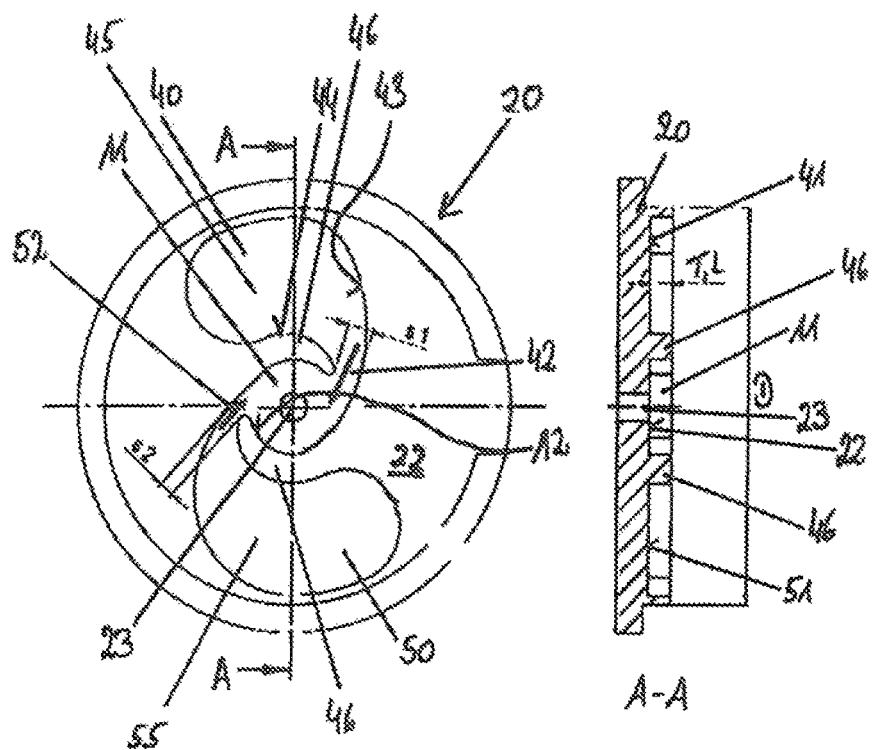
FIG. 2a shows a top view of a nozzle plate with an integrated mixing chamber for a nozzle according to the invention according to a further preferred exemplary embodiment.
FIG. 2b shows a cross-sectional view of the nozzle plate according to FIG. 2a along line A-A.

The design and dimensions of mixing chamber 11 and inlet chambers 45, 55 with their inlet openings 42, 52 substantially correspond to the design according to FIGS. 2a to 3. In addition, in the case of the exemplary embodiment according to FIGS. 4a and 4b, it is provided that nozzle 1 has at least one temperature control line (not shown) which ends in nozzle plate 20 in a temperature control duct 90. This enables temperature control of the fluids both before the mixing operation and during the mixing operation. Temperature control ducts 90 are accommodated as substantially rectangular recesses in nozzle plate 20. The rectangular recesses can have rounded corners. The temperature control line can extend parallel to the supply lines and/or supply ducts 30, 40, 50 from the proximal end of the surgical instrument into nozzle plate 20 of nozzle 1. As a result, it is already possible to perform temperature control for the fluids in the region of the supply of the fluids. A temperature control line can comprise two lumens. One for the supply and one for the return of the temperature control medium. It is also possible that two separate temperature control lines are used for the supply and return of the medium. The surgical instrument can comprise several temperature control lines.

In this manner, the supply lines and nozzle plate 20 and thus the fluid mixture produced in mixing chamber 11 can be subjected to temperature control prior to exiting through nozzle opening 23. For example, the fluid mixture can be heated in order to reduce the viscosity of the fluid mixture.

A reduced viscosity is expedient in the case of the supply of cells since in this manner shear forces in mixing chamber 11 are reduced. Damage to the cells is thus avoided. In other words, a temperature increase of the produced fluid mixture and thus an associated change in viscosity contribute to careful transport of cells. It can furthermore be brought about by an increase in temperature that the crosslinking of at least two fluids to be mixed with one another is accelerated. The adhesion of the fluids mixed with one another to an existing target tissue can thus be positively influenced. Vice versa, the temperature control lines which end in temperature control ducts 90 can be used for cooling the supply lines and nozzle plate 20 and as a result mixing chamber 11 and thus the crosslinking of two substances to be mixed can be slowed down. This can have advantages if, for example, it is desired that the crosslinking only arises on contact with a target tissue.

Instead of one temperature control duct 90 or several temperature control ducts 90, an electric heater can be integrated into nozzle plate 20.

FIGS. 5a and 5b show a further exemplary embodiment of a nozzle plate 20 for a nozzle according to the invention. The structure of nozzle plate 20 is similar to the structure of the nozzle plate according to the preceding exemplary embodiments. It is nevertheless provided in the case of this variant that, in addition to axially discharging first supply duct 30, a total of three further supply ducts discharge laterally into mixing chamber 11. The supply ducts have at their distal end portions drop-shaped inlet chambers 45, 55, 65, as are already known from the previous exemplary embodiments. The transition to mixing chamber 11 is achieved via inlet openings 42, 52, 53, with inlet openings 42, 52, 53 discharging into mixing chamber 11 directly in front of nozzle 23. In concrete terms, inlet openings 42, 52, 53 at distal end surface 22 reach mixing chamber 11 or have deflection surfaces 41, 51, 54 which are formed in the same plane as distal end surface 22 or are formed by distal end surface 22. Three inlet openings 42, 52, 53 have different widths s. The determination of the mixing parameters of the supplied fluids is independent of the number of supply lines or supply ducts. The conditions of a preferred mixing of the supplied fluids are described above.

In the case of this additionally disclosed variant of the nozzle, it is provided that the opening surface of inlet openings 42, 52, 53, in particular width s of inlet openings 42, 52, 53 is selected to be different for each inlet opening 42, 52, 53 so that as a result the average flow speed of the fluids on entry into mixing chamber 11 can be determined.

The fluid jet leaves nozzle 1 at the distal end of nozzle opening 23. It is possible that the supply lines and as a result supply ducts 30, 40, 50 can be connected in each case to a separate pump. Each pump is preferably provided with a flow or pressure regulator. The requirements for producing a fluid jet which is in a conical or spot jet form are described above.

Figure 6:
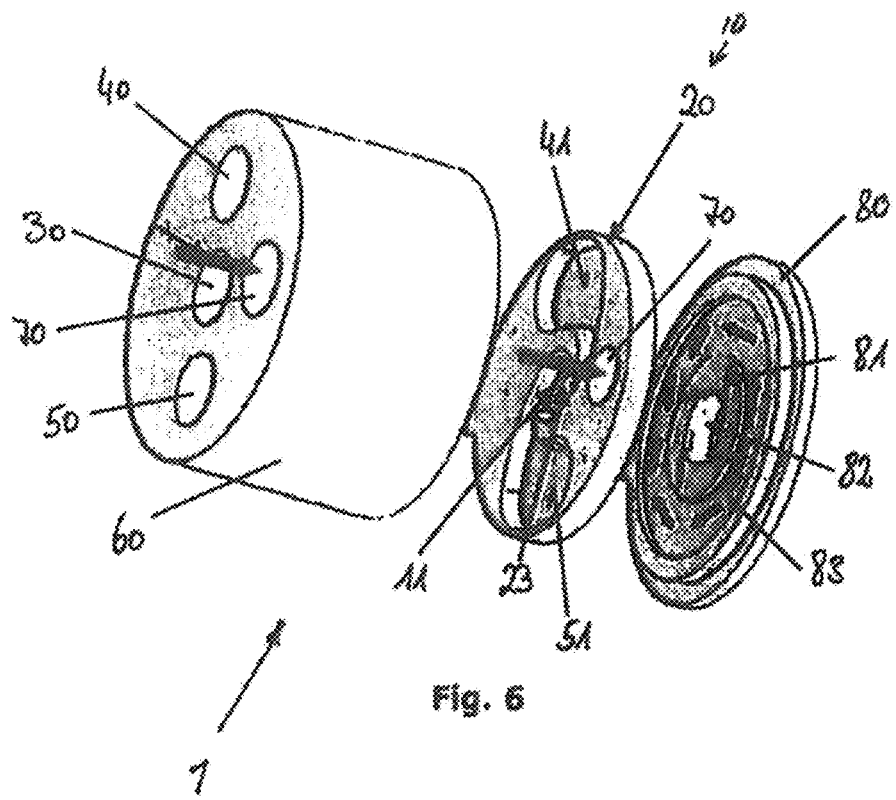
FIG. 6 shows a perspective view of a nozzle according to the invention according to a further preferred exemplary embodiment, wherein an atomiser plate is provided.

It can be advantageous if nozzle 1 is additionally provided with a device for subsequent atomisation. FIG. 6 shows such an expanded nozzle 1. In the case of this exemplary embodiment, the nozzle is formed in several pieces and comprises a duct carrier 60 and a nozzle plate 20 into which mixing chamber 11 is integrated. Nozzle plate 20 therefore has a mixing chamber portion or is formed integrally, i.e. in one piece, with mixing chamber plate 10. The structure of nozzle plate 20 and of duct carrier 60 corresponds substantially to the structure in the case of the previous exemplary embodiments. In the case of the exemplary embodiment according to FIG. 6, this is supplemented by a gas supply duct 70 which is formed in nozzle 1.

Gas supply duct 70 runs parallel to supply ducts 30, 40, 50. Gas supply duct 70 extends through duct carrier 60 and nozzle plate 20 or penetrates through both. As a result, gas supply duct 70 runs parallel to mixing chamber 11 and/or to nozzle opening 23. An atomiser plate 80 is provided adjoining nozzle plate 20. Atomiser plate 80 has a central atomiser opening 82 which is flush with nozzle opening 23. Atomiser opening 82 is arranged coaxially to nozzle opening 23. Atomiser opening 82 is likewise arranged coaxially to mixing chamber 11 and to first supply duct 30. An annular groove 83 runs around atomiser opening 82, annular groove 83 being arranged as an annular recess on one proximal side of atomiser plate 80. Annular groove 83 is in fluid connection with gas supply duct 70. The gas which flows in via gas supply duct 70 is distributed evenly across annular groove 83.

Atomiser ducts 81 are arranged between annular groove 83 and atomiser opening 82. Atomiser ducts 81 discharge tangentially into circular atomiser opening 82. Atomiser ducts 81 and annular groove 83 are delimited on three sides by elements of atomiser plate 80. A fourth side of atomiser duct 81 and annular groove 83 is delimited in the mounted state by a distal outer surface of nozzle plate 20.

In another design of the expanded nozzle (not shown), the distal end surface of nozzle plate 20 can comprise annular groove 83 and atomiser ducts 81. The features described above of atomiser plate 80 are integrated in nozzle plate 20. Atomiser ducts 81 and annular groove 83 are then delimited on three sides by elements of nozzle plate 20. Atomiser plate 80 contains in this case only atomiser opening 82. The proximal surface of atomiser plate 80 then form a cover of annular groove 83 and of atomiser ducts 81 and seal these off distally.

The cross-sectional surface of an atomiser duct 81 is significantly smaller than the cross-sectional surface of annular groove 83. Even the sum of the cross-sectional surfaces of atomiser ducts 81 is significantly smaller than the cross-sectional surface of annular groove 83. This enables a consistent gas supply or a consistent exit of gas from atomiser opening 82 although only one gas supply duct 70 is arranged in nozzle 1. As a result of the large cross-sectional surface of annular groove 83 in comparison to the small total cross-sectional surface of atomiser ducts 81, the supplied gas is distributed evenly in annular groove 83, independently of the arrangement of gas supply duct 70. In other words, gas supply duct 70 does not have to be arranged coaxially on nozzle 1, it can be arranged offset radially to the outside and nevertheless a consistent exit of gas out of atomiser opening 82 is ensured.

Figure 7:
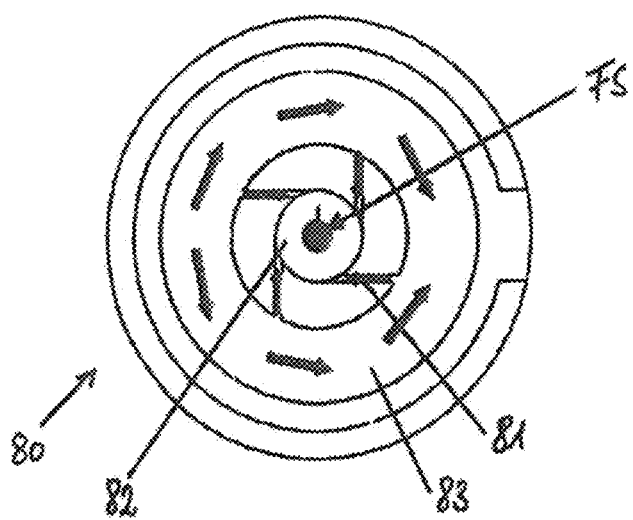
FIG. 7 shows a top view of the atomiser plate according to FIG. 6.

On the other hand, the gas is accelerated prior to entry into atomiser opening 82 by reducing the flow cross-section during the transition from annular groove 83 into atomiser ducts 81. The accelerated gas strikes fluid jet FS which preferably has the form of a conical jet. The droplets already formed by the conical jet are thus further dissipated in fluid jet FS so that an aerosol is substantially formed. Moreover, the tangential gas supply enables an influencing of the spraying angle. In concrete terms, the conical jet can be further widened. It is expedient for the functionality of atomiser plate 80 if, as is shown in FIGS. 6 and 7, atomiser opening 82 has a larger cross-sectional diameter than nozzle opening 23.

A plurality of atomiser ducts is required so that the advantages described above can exhibit their full effect. In the case of the exemplary embodiment according to FIGS. 6 and 7, four atomiser ducts 81 are provided. The gas which flows via gas supply duct 70 and annular groove 83 into atomiser ducts 81 in the region of atomiser opening 82. A substantially cylindrically formed gas flow which surrounds fluid jet FS is thus generated around fluid jet FS.

As explained above, a transfer of cells with a relatively high survival rate is enabled with the nozzle according to the invention which is preferably part of a water jet applicator. The nozzle therefore ensures careful transport and careful application of cells. To this end, it is contemplated to feed cells via first supply duct 30 into mixing chamber 11, wherein first supply duct 30 discharges axially into mixing chamber 11 and is aligned coaxially to nozzle opening 23. The cells carried along in the first fluid jet thus do not undergo any deflection which could contribute to the occurrence of shear forces and to damage to the cells. The cells are therefore protected by the linear flow profile. The cells can be applied separately via first supply duct 30. It is nevertheless preferably provided to mix in a carrier fluid in mixing chamber 11. The carrier fluid can be, for example, medical water, organic substances such as blood plasma, blood serum or organic adhesives, biological substances such as enzymes, coagulation factors and/or further blood components, solutions, suspensions, emulsions with medical and/or pharmaceutical components or a common salt solution. In this manner, substantially one nozzle for a water jet applicator is provided which enables careful cell transport. The transport of cells can be quantity-controlled in a pressure-restricted, precise and easy manner by means of water jet technology.

A key aspect of the invention lies in the further supply ducts, in particular second and third supply duct 40, 50, not only discharging laterally into mixing chamber 11, rather the cross-sectional diameter or the cross-sectional dimension of second and/or third supply duct 40, 50 is reduced up until entry into mixing chamber 11. It is thus achieved that the flow speed of the fluid fed in respective supply duct 40, 50 is increased. As a result, the static pressure of the supplied fluids falls. In this regard, inlet chamber 45, 55 and inlet opening 42, 52 forms in each case an acceleration section for the fluid fed in supply duct 40, 50. A further contribution to careful cell transport is made in that the individual ducts, in particular first supply duct 30, second supply duct 40 and third supply duct 50, are jointly fed into mixing chamber 11. The mixing of the individual fluids is carried out in mixing chamber 11. As a result of this, the section in which the fluid which feeds cells is exposed to shear forces or mixing forces is extremely small, which protects the cells. Moreover, as a result of this short section in the nozzle or the short time in which the fluids are mixed in the nozzle, the crosslinking of the different substances is also largely, ideally completely suppressed. A nozzle according to the invention is formed to be small and compact. The crosslinking of the mixed fluids mainly takes place outside the nozzle. As a result, a blocking of the nozzle is largely prevented. In addition, an increase in the shear forces is avoided as a result of the crosslinking. The same applies to the arrangement of nozzle opening 23 which is arranged immediately after mixing chamber 11. In concrete terms, this is achieved according to the invention in that lateral inlet openings 42, 52 directly adjoin the surface from which nozzle opening 23 also emerges. In this exemplary embodiment, this corresponds to distal end surface 22 of mixing chamber 11.

There are a variety of possible applications for the nozzle according to the invention. For example, cells can be fed to organs of the gastrointestinal tract, for example, the stomach, the bowel or the oesophagus with the nozzle according to the invention. In principle, organs, in particular the outer walls of organs have a tissue structure composed of several cell layers which are to some extent different and lie on top of one another. The inner organ wall comprises in particular the tissue cell layers of the mucosa, the submucosa, the muscularis and/or the serosa. The individual cell layers have different functional objectives. In order to treat individual damaged points in the organ wall, different types of cell should therefore be supplied.

The treatment of such organ walls can be carried out particularly efficiently with the nozzle according to the invention which is formed substantially as a multi-substance nozzle. Since the nozzle according to the invention has several supply ducts 30, 40, 50, different substances and/or different fluid mixtures can be applied during a treatment procedure via the nozzle opening. Individual supply ducts 30, 40, 50 can be activated independently of one another. Different substances or mixtures of different substances can thus be supplied at different times during medical treatment.

A surgical instrument with a nozzle according to the invention can furthermore be connected or connectable to a surgical apparatus. The surgical apparatus can have an open-loop or closed-loop control unit with which different fluid supply pressures or different fluid volumetric flows can be set. A fluid supply pressure in the range from 2.5 to 60 bar, in particular in the range from 5 bar to 40 bar is preferably set for spraying, in particular for conical jet operation. For application of an aerosol or an aerosol plasma, it is advantageous if the fluid supply pressures are set between 2 bar and 10 bar. Preferred volumetric flows for the supplied fluid in supply ducts 30, 40, 50 for spraying are in the range from 5 ml/min to 40 ml/min, in particular in the range from 10 ml/min to 30 ml/min, preferably in the range from 15 ml/min to 25 ml/min. For needle-free injection of liquids or fluids, it is advantageous if the volumetric flow in at least one of supply ducts 30, 40, 50 is set between 5 ml/min and 110 ml/min, in particular between 10 ml/min and 100 ml/min, in particular between 20 ml/min and 90 ml/min. It has been shown to be advantageous for the supply of aerosol plasma if the volumetric flow in at least one of supply ducts 30, 40, 50 is 0.2 ml/min to 5 ml/min, in particular 0.3 ml/min to 3 ml/min, preferably 0.5 ml/min to 1 ml/min.

Figure 8B:
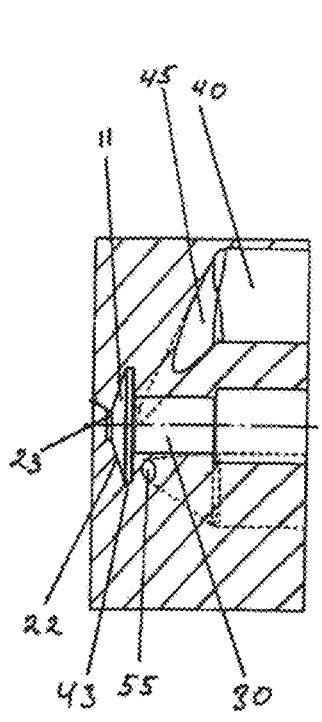
FIG. 8b shows a cross-sectional view of nozzle 1 according to FIG. 8a along line D-D.
Figure 8A:
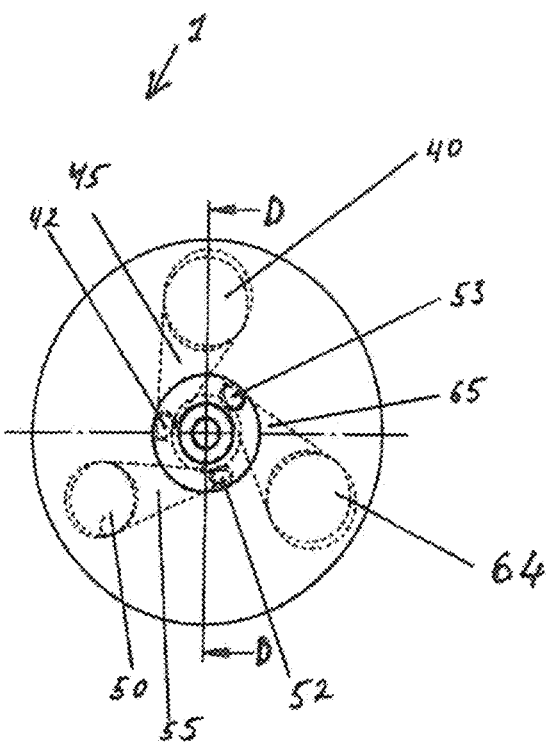
FIG. 8a shows a top view of a nozzle 1 formed in one piece and seamlessly according to a further preferred exemplary embodiment.

FIG. 8 shows an exemplary embodiment in which nozzle 1 is embodied in one piece. In this case, nozzle opening 23, mixing chamber 11, inlet chambers 45, 55, 65, inlet openings 42, 52, 53 and supply ducts 30, 40, 50, 64 are embodied integrally in one component. According to the invention, in the case of this embodiment of nozzle 1, the fluid flows through edge-free deflections up into the mixing chamber, wherein supply ducts 40, 50, 64, which are offset radially to the outside, are formed to be tubular according to the invention. In contrast to the exemplary embodiments described above, in which supply ducts 40, 50, in particular their deflection regions are formed by surface portions joined to one another, in the embodiment according to FIG. 8, these deflection regions are formed by cylindrical, edge-free line portions. This enables a gradual deflection of the fluid to be supplied even in the case of a change in the direction of flow by up to 90 degrees. As a result, the fluid to be supplied can be supplied to mixing chamber 11 in a careful manner. The configuration of supply ducts 40, 50, 64 enables a continuous, gradual deflection of the direction of flow of the fluids which flow through these supply ducts from the proximal end of nozzle 1 up until entry into mixing chamber 11. Although the direction of flow changes from the distal end of supply ducts 40, 50, 64 up to the mixing chamber by up to 90 degrees, the supply ducts on this entire section have no points which produce an abrupt deflection of the direction of flow. The supply ducts are exclusively provided with radii, sharp-edged corners are avoided. According to the invention, the supply ducts have on their path to mixing chamber 11 angles which are smaller than 90 degrees, preferably between 40 and 65 degrees, in particular preferably between 10 and 30 degrees.

The configuration of supply ducts 40, 50 and 64 is described by way of example on the basis of supply duct 40 and also applied to supply ducts 50, 64 and any others present. Supply duct 40 extends from the proximal end of nozzle 1 into mixing chamber 11. It comprises inlet chamber 45 and inlet opening 42. Inlet chamber 45 which comprises inlet opening 42 is formed in the form of an inclined circular truncated cone. The truncated cone tapers in the direction of inlet opening 42. This truncated cone discharges into mixing chamber 11 tangentially in the region of inlet opening 42 at an angle in relation to the longitudinal axis of nozzle 1. In this case, inlet opening 42 of supply duct 40 is offset radially to the outside in relation to supply duct 30 or to nozzle opening 23. Inlet opening 42 forms a transition into mixing chamber 11 in expedient flow conditions. This transition can, for example, end in proximal end surface 21 of mixing chamber 11. It can, however, also form a transition to outer lateral surface 43 of mixing chamber 11 in expedient flow conditions. In this case, the diameter of inlet opening 42 can be larger than the width of lateral surface 43. This then has the advantage that inlet opening 42 forms a transition partially in proximal end surface 22, partially in lateral surface 43 and possibly partially in distal end surface 21 of mixing chamber 11. The line of the centre of gravity (centre line) of inlet chamber 45 is arranged at an angle to proximal end surface 21 of mixing chamber 11. This angle is smaller than 90 degrees, preferably at most 65, preferably at most 50 degrees. During the transition of inlet chamber 45 to proximal end surface 21 of mixing chamber 11, the profile of the line of the centre of gravity of inlet chamber 45 is arranged such that a perpendicular projection of this line of the centre of gravity onto proximal end surface 21 tangentially forms a transition to a circle arranged concentrically to nozzle opening 23. The design of inlet chamber 45 as a part of the supply duct with a consistently narrowing cross-section brings about an increase in the flow speed of the fluid, which flows through supply duct 40, up until entry into mixing chamber 11. The features described in the exemplary embodiments according to FIGS. 1 to 7 of a mixing chamber and nozzle opening 23 also apply to mixing chamber 11 and nozzle opening 23 according to FIG. 8.

The configuration and arrangement according to the invention of supply duct 40 has the advantage for the supplied fluid that the gradual deflections lead to a slight drop in pressure in the fluid. This enables a low conveying pressure which enables careful supply of the fluid. As a result of the gradual deflections according to the invention of the supply duct, the impulse change forces on the fluid generated during changes in direction of the fluid are reduced which additionally enables careful transport of the fluid to mixing chamber 11.

Figure 9A:
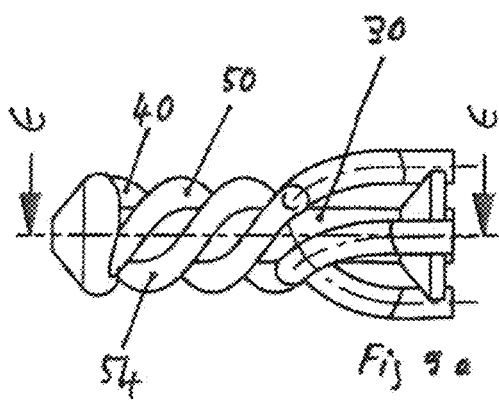
FIG. 9a shows a perspective view of a nozzle 1 according to the invention according to a further preferred exemplary embodiment, wherein the supply ducts are formed to be tubular
Figure 9B:
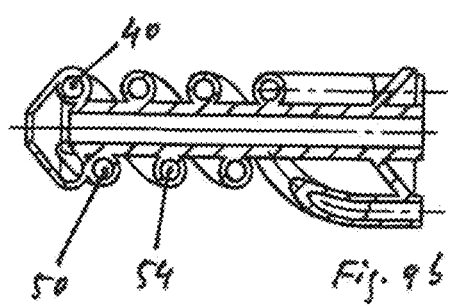
FIG. 9b shows a cross-sectional view of nozzle 1 according to FIG. 9a along line E-E.

FIGS. 9a and 9b show an exemplary embodiment according to the invention with the same structural features and the same advantages as the exemplary embodiment according to FIG. 8. In contrast to the exemplary embodiment according to FIG. 8, supply ducts 40, 50, 64 are formed by tubular lines in the case of the exemplary embodiment according to FIG. 9. FIGS. 9a and 9b also show a nozzle 1 formed in one piece, the flow properties of which of the supplied fluids are identical to the flow properties of an exemplary embodiment according to FIG. 8.

One-piece multi-lumen nozzles can be produced, for example, by laser sintering methods.

LIST OF REFERENCE NUMBERS

1 Nozzle
10 Mixing chamber plate
11 Mixing chamber
12 Inner circumferential surface
20 Nozzle plate
21 Proximal end surface
22 Distal end surface
23 Nozzle opening
24 Shoulder
30 First supply duct
40 Second supply duct
41, 51, 54 Deflection surface
42, 52, 53 Inlet opening
43 Outer lateral surface
44 Inner lateral surface
45, 55, 65 Inlet chamber
46, Web
50 Third supply duct
64 Further supply duct
60 Duct carrier
61 Rail
70 Gas supply duct
80 Atomiser plate
81 Atomiser duct
82 Atomiser opening
83 Annular groove
90 Temperature control duct
s Width of the inlet opening
s1 Width of first inlet opening 42
s2 Width of second inlet opening 52
T Depth of inlet opening 42, 52
L Length of mixing chamber 11
FS Fluid jet

What is claimed is:
1. Nozzle for the supply of biological material comprising:

a mixing chamber (11) which is delimited by a proximal end surface (21) and a distal end surface (22) spaced apart from the proximal end surface (21), at least one nozzle opening (23) which is formed in the distal end surface (22), at least two supply ducts (30, 40, 50) which discharge into the mixing chamber (11), a first supply duct (30) is arranged in the proximal end surface (21) and configured to discharge into the mixing chamber (11) coaxially to the nozzle opening (23), and a second supply duct (40) including an inlet opening (42) which discharges into the mixing chamber (11) laterally from and tangentially to an axis passing through the at least one nozzle opening (23) at the distal end surface (22) wherein the inlet opening (42) discharges into the mixing chamber (11) in a plane orthogonal to the axis passing through the at least one nozzle opening (23).

2. Nozzle according to claim 1, wherein the mixing chamber (11) has a length L which is at most 500 μm.

3. Nozzle according to claim 1, wherein the inlet opening (42) has a depth T which corresponds to length L of the mixing chamber (11).

4. Nozzle according to claim 1, wherein the distal end surface (22) of the mixing chamber (11) is arranged perpendicular to a longitudinal axis of the second supply duct (40).

5. Nozzle according to claim 1, wherein the inlet opening (42) has a rectangular cross-sectional profile or tapers in a direction of the mixing chamber (11).

6. Nozzle according to claim 5, wherein the inlet opening (42) has in particular two curved lateral surfaces (43, 44) which converge at the mixing chamber (11).

7. Nozzle according to claim 6, wherein an outer lateral surface (43) of the inlet opening (42) forms a continuous transition into an inner circumferential surface (12) of the mixing chamber (11).

8. Nozzle according to claim 1, further comprising at least one third supply duct (50) with an additional lateral inlet opening (52), which discharges laterally into the mixing chamber (11) at the distal end surface (22).

9. Nozzle according to claim 1, wherein one or more of the supply ducts (30, 40, 50), the mixing chamber (11), and the nozzle opening (23) are formed in one piece or several pieces.

10. Nozzle according to claim 1, wherein the supply ducts (30, 40, 50) are formed in a duct carrier (60) or the nozzle opening (23) is formed in a nozzle plate (20), wherein the mixing chamber (11) is formed in the nozzle plate (20) or in a mixing chamber plate (10) which is arranged between the nozzle plate (20) and the duct carrier (60).

11. Nozzle according to claim 1, further comprising at least one temperature control duct (90) configured to provide temperature control for a fluid flowing through at least one supply duct (30, 40, 50), wherein the temperature control duct (90) connects a supply line and a return line in such a manner that a closed temperature control circuit is formed.

12. Nozzle according to claim 1, further comprising at least an atomiser plate (80) connected distally to the nozzle plate (20) and having an atomiser opening (82) arranged coaxially to the nozzle opening (23), wherein at least one atomiser duct (81) is formed in the atomiser plate (80), connects the atomiser opening (82) to a gas supply duct (70) and preferably discharges tangentially into the atomiser opening (82).

13. Nozzle for medical purposes comprising:
a mixing chamber (11), which is delimited by a proximal end surface (21) and a distal end surface (22) spaced apart from the proximal end surface (21), and
at least one nozzle opening (23) which is arranged in the distal end surface (22),
wherein the mixing chamber (11) has a substantially cylindrical inner contour with at least two inlet openings (42, 52) which discharge into the mixing chamber (11) laterally from and tangentially to an axis passing through the at least one nozzle opening (23), which inlet openings (42, 52) are fluid-connected to a supply duct (40, 50),
wherein the at least two inlet openings (42) discharge into the mixing chamber (11) in a plane orthogonal to the axis passing through the at least one nozzle opening (23), and
wherein the inlet openings (42, 52) have different or the same cross-sectional surfaces.

14. Nozzle according to claim 13, wherein a cross-sectional surface of the inlet opening (42, 52) is formed to be smaller than a cross-sectional surface of the supply line (30).

15. Nozzle according to claim 13, wherein a ratio of the cross-sectional surfaces of the inlet openings (42, 52) corresponds to a ratio of volumetric flows of at least two fluids which flow with different or same volumetric flows into the mixing chamber (11), so that the fluids flow into the mixing chamber (11) with a substantially same average entry speed.

* * * * *